US00PP10283P

United States Patent [19]

Zary

[11] Patent Number: Plant 10,283

[45] Date of Patent: Mar. 17, 1998

[54] FLORIBUNDA ROSE PLANT NAMED 'JACYELSH'

[75] Inventor: Keith W. Zary, Thousand Oaks, Calif.

[73] Assignee: Bear Creek Gardens, Inc., Medford, Oreg.

[21] Appl. No.: 759,936

[22] Filed: Dec. 3, 1996

[51] Int. Cl.[6] ..... A01H 5/00

[52] U.S. Cl. ..... Plt./24

[58] Field of Search ..... Plt./24, 15

*Primary Examiner*—Howard J. Locker

*Attorney, Agent, or Firm*—Klarquist Sparkman Campbell Leigh & Whinston, LLP

[57] ABSTRACT

A new and distinct variety of rose plant of the floribunda class, having a vigorous, upright habit of growth; resistance to powdery mildew and rust; its dark green, glossy, leathery foliage; continuous blooming during the growing season; and ease of propagation from softwood cuttings.

1 Drawing Sheet

The present invention relates to a new and distinct variety of rose plant of the floribunda class which was originated by me by crossing two unnamed seedlings.

The primary objective of this breeding was to produce a new rose variety having the bright yellow flowers and healthy, glossy, dark green foliage of the unnamed yellow floribunda seedling female parent combined with the bright yellow flowers, glossy foliage and tall, vigorous growth habit of the unnamed yellow shrub male parent. The objective was substantially achieved, along with other desirable improvements, as evidenced by the following unique combination of characteristics that are outstanding in the new variety and that distinguish it from its parents, as well as from all other varieties of which I am aware:

1. Vigorous, upright habit of growth;
2. Resistance to powdery mildew and rust;
3. Dark green, glossy, leathery foliage;
4. Continuous blooms during the growing season; and
5. Ease of propagation from softwood cuttings.

Asexual reproduction of this new variety by softwood and hardwood cuttings, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—An unamed seedling.

*Pollen parent.*—An unnamed seedling.

Classification:

*Botanical.*—*Rose hybrida.*

*Commercial.*—Floribunda.

FLOWER

Observations made from specimens grown from January 1995 through September 1996 in a garden environment at Somis, Calif.

Blooming habit: Continuous.

Bud:

*Size.*—1½ inches long when the petals start to unfurl.

*Form.*—The bud form is long, pointed ovoid.

*Color.*—When sepals first divide, bud color is Yellow-Orange Group 23B with the bud tipped in Red Group 43B. When half blown, both the upper and lower sides of the petals are Yellow-Orange Group 14C.

*Sepals.*—Color: Green Group 138B. Surface texture: Covered in many fine hairs. There are three lightly appendaged sepals. There are two unappendaged sepals with hairy edges.

*Receptacle.*—Color: Green Group 137C. Shape: Funnel. Size: Medium (⅜ inch×¼ inch). Surface: Smooth, with some fine hairs.

*Peduncle.*—Length: Short (1¾ inches to 2 inches). Surface: Smooth, with a few fine hairs. Color: Medium green. Strength: Stiff, erect.

Bloom:

*Size.*—Medium. Average open size is 3½ inches.

*Borne.*—Singly and several together, in flat clusters of 5 to 7 flowers.

*Stems.*—Medium, strong. Average length is about 12 to 16 inches.

*Form.*—When first open: Cupped to globular. Permanence: Retains its form to the end.

*Petalage.*—Number of petals under normal conditions: 15 to 20.

*Color.*—The upper and reverse sides of the petals are Yellow-Orange Group 14C. The color of the petals intensifies to Yellow-Orange Group 14B at the petal base. The major color on the upper side is Yellow-Orange Group 14C.

*Variegations.*—None.

*Discoloration.*—The general tonality at the end of the first day: No change. At the end of the third day: Some fading under bright sun to Yellow-Orange Group 14D.

*Fragrance.*—Moderate.

Petals:

*Texture.*—Thick.

*Shape.*—Deltoid.

*Form.*—Tips slightly recurved.

*Arrangement.*—Imbricated, with few petaloids in the center.

*Persistence.*—Drop off cleanly.

*Lastingness.*—On the plant: Short (3 days). As a cut flower: Short (5 days).

Reproductive parts:

*Anthers.*—Size: Large. Quantity: Many. Color: Yellow. Arrangement: Regular around styles.
*Filaments.*—Color: Yellow.
*Pollen.*—Color: Gold yellow.
*Styles.*—Color: Red.
*Stigmas.*—Color: Greenish white.

Form: Bush.

Growth: Very vigorous; upright; branching; vertical grower. Will attain 4½ feet in height and be 3 feet wide after one year of growth in Southern California.

Foliage:
*Number of leaflets on normal mid-stem leaves.*—5 or 7.
*Size.*—Medium (5 inches×4 inches).
*Quantity.*—Abundant.
*Color.*—New foliage: Greyed Red Group 178A upper and lower surfaces. Old foliage: Upper surface Green Group 139A; lower surface Green Group 137C.

Leaflets:
*Shape.*—Pointed oval.
*Texture.*—Upper side: Leathery, glossy.
*Edge.*—Serrated.
*Serration.*—Single, small.
*Petiole rachis.*—Color: Green.
*Petiole underside.*—Smooth.
*Stipules.*—Long (up to 1 inch); serrated.
*Disease resistance.*—Resistant to mildew and rust under normal growing conditions at Somis, Calif.

Wood:
*New wood.*—Color: Light green. Bark: Smooth.
*Old wood.*—Color: Green. Bark: Smooth.

Prickles:
*Quantity.*—On main canes from base: Ordinary. On laterals from main canes: Ordinary.
*Form.*—Long; broad; hooked downward.
*Color when young.*—Red.

Small prickles:
*Quantity.*—On main stalks: None. On laterals: None.

I claim:

1. A new and distinct variety of rose plant of the floribunda class, substantially as herein shown and described, characterized particularly as to novelty by the unique combination of its vigorous, upright habit of growth; its resistance to powdery mildew and rust; its dark green, glossy, leathery foliage; its continuous blooming during the growing season; and its ease of propagation from softwood cuttings.

* * * * *

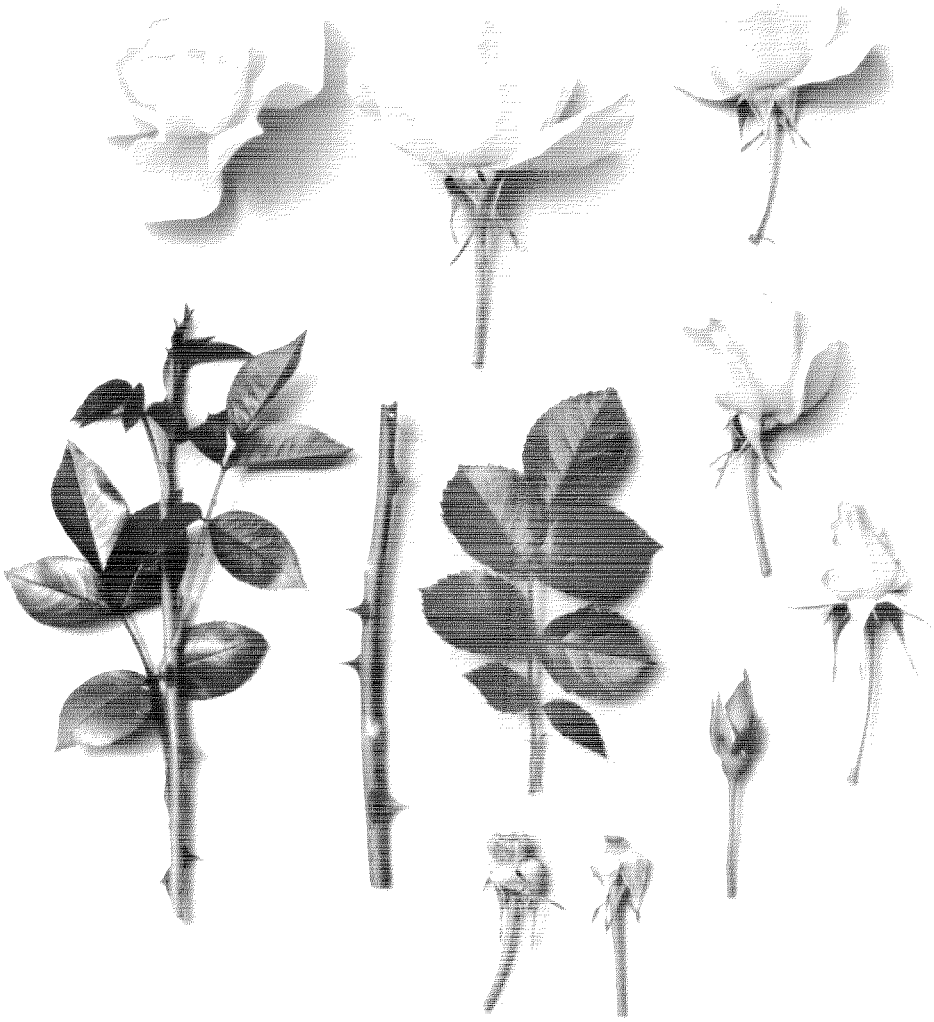
J.A.C. Welsh